United States Patent [19]

Sato

[11] Patent Number: 4,744,350
[45] Date of Patent: May 17, 1988

[54] SCALP MASSAGER HAVING RESILIENTLY BIASED ROLLER WITH OPTIONAL INTERNAL MAGNET

[76] Inventor: Atsuhiko Sato, 10-20, Matsubara 5-chome, Soka, Saitama, Japan

[21] Appl. No.: 936,759

[22] Filed: Dec. 2, 1986

[30] Foreign Application Priority Data

Dec. 9, 1985 [JP] Japan .................. 60-188473[U]

[51] Int. Cl.⁴ ............................................. A61H 15/00
[52] U.S. Cl. ..................................... 128/57; 128/24.3
[58] Field of Search .................... 128/24.3, 24.2, 24.1, 128/57, 67

[56] References Cited

U.S. PATENT DOCUMENTS

| 572,341 | 12/1896 | Gibbs | 128/57 |
|---|---|---|---|
| 733,977 | 7/1903 | Lagerstrom et al. | 128/57 |
| 1,772,501 | 8/1930 | Shelton | 128/24.2 |
| 2,248,525 | 7/1941 | Fleissner | 128/57 |
| 2,515,524 | 7/1950 | Manzel | 128/57 |
| 2,737,672 | 3/1956 | Weinman | 128/57 |
| 2,827,895 | 3/1958 | Clohecy et al. | 128/67 |
| 3,107,665 | 10/1963 | Nordgren | 128/67 |
| 4,067,324 | 1/1978 | Greenawalt | 128/57 |
| 4,150,667 | 4/1979 | Takeuchi | 128/57 |
| 4,571,768 | 2/1986 | Kawashima | 128/1.3 |

FOREIGN PATENT DOCUMENTS

| 2480118 | 10/1981 | France | 128/57 |
|---|---|---|---|
| 563769 | 7/1975 | Switzerland | 128/57 |
| 16783 | 10/1899 | United Kingdom | 128/57 |
| 195292 | 3/1923 | United Kingdom | 128/57 |

Primary Examiner—Charles A. Pearson
Assistant Examiner—Tonya Lamb
Attorney, Agent, or Firm—Parkhurst & Oliff

[57] ABSTRACT

A scalp massager has a main body provided on the rear end thereof with a grip portion, a base portion, a pair of supporting arms projecting laterally from the base portion and spaced from each other in the longitudinal direction of the base portion, a roller member rotatably mounted between the arms for rotation about an axis substantially parallel to the longitudinal axis of the base portion, the roller member being provided on the outer peripheral surface thereof with a multiplicity of scalp stimulating projections, and compression springs for resiliently biasing the roller member away from the grip portion. The user grips the grip portion and lightly presses the roller member onto his head, and moves the massager back and forth so that the roller member rolls on the scalp with the result that the projections stimulate blood vessels under the scalp so as to enhance the blood stream. The roller member, which is resiliently urged by the compression springs, can gently and uniformly contact the scalp so as to moderately stimulate the head without any risk for the scalp to be damaged.

9 Claims, 2 Drawing Sheets

SCALP MASSAGER HAVING RESILIENTLY BIASED ROLLER WITH OPTIONAL INTERNAL MAGNET

BACKGROUND OF THE INVENTION

1. Field of the Invention

The present invention relates to a scalp massager for promoting growth of hair.

2. Description of the Prior Art

It is well known that premature alopecia and thin hair are generally attributable to undernourishment of hair matrix cells and hair roots and various proposals and attempts have been made to prevent or treat premature alopecia and thin hair. Such proposals and attempts are generally sorted into two types: namely, chemical methods which rely upon nourishment of the hair matrix cells and hair roots, and physical methods which are intended for increasing the blood stream under the scalp by suitably stimulating the scalp.

Physical stimulation is typically effected by means of a hair brush. It is possible to enhance the blood stream by lightly tapping or patting the scalp by the ends of the bristles of the brush. This method, however, involves a risk in that the scalp tends to be damaged particularly when the bristles of the brush are too rigid or too thin. On the contrary, too soft or flexible bristles cannot provide sufficient stimulating effect. Thus, the rigidity of the brush bristles have to be determined within an extremely limited range, which makes the production of the brushes very difficult. Furthermore, the bristles of the brush tend to lose their resiliency in a short period of time, with the result that the brush becomes unusable shortly. It is to be pointed out also that the stimulation of the scalp requires an exquisite control of the tapping force.

Under these circumstances, the present invention aims at providing a physical scalp stimulating means which can overcome the above-described problems of the prior art.

SUMMARY OF THE INVENTION

Accordingly, an object of the present invention is to provide a scalp massager which is easy to produce and which can withstand a long use without any risk for the scalp to be damaged.

To this end, according to the present invention, there is provided a scalp massager comprising: a main body provided on the rear end thereof with a grip portion; a pair of supporting arms projecting laterally from the end of the main body remote from the grip portion and spaced from each other in the longitudinal direction of the main body; a roller member rotatably mounted between the arms for rotation about an axis substantially parallel to the longitudinal axis of the grip portion, the roller member being provided on the outer peripheral surface thereof with a multiplicity of scalp stimulating projections; and resilient means for resiliently biasing the roller member away from the grip portion.

In a preferred form of the present invention, the arms are hollow as to receive both ends of the shaft of the roller member, and compression springs are loaded between anchoring portions in respective arms and the associated ends of the shaft of the roller member in such a manner as to resiliently urge the roller member away from the grip portion.

In another preferred form of the present invention, each compression spring is disposed in a guide frame which in turn is provided between the anchoring portion in each arm and the associated end of the roller member.

In still another preferred form of the present invention, the axis of rotation of the roller member is inclined by a predetermined angle with respect to the longitudinal axis of the grip portion, so that the user may easily stimulate the scale while holding the grip portion by his hand.

The above and other objects, features and advantages of the invention will become clear from the following description of the preferred embodiment when the same is read in conjunction with the accompanying drawings.

DESCRIPTION OF THE PREFERRED EMBODIMENT

Figure 1:
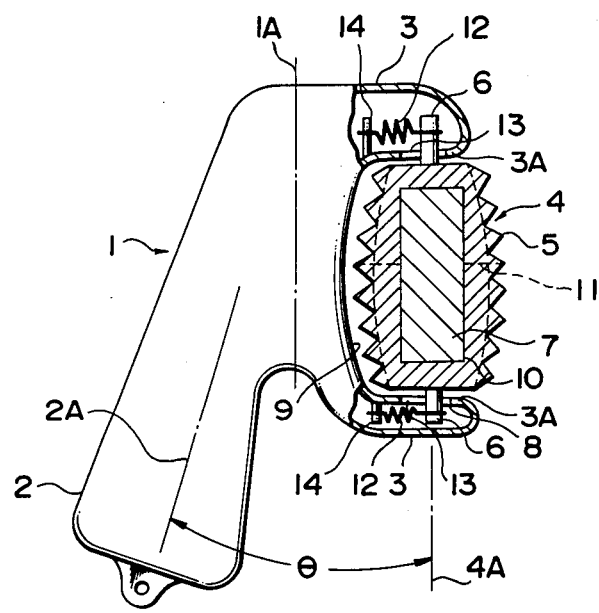
FIG. 1 is a fragmentary sectional view of a preferred embodiment of the scalp massager in accordance with the present invention.

Referring first to FIG. 1, an embodiment of the scalp massager in accordance with the present invention has a main body 1 which is provided on the rear end thereof with a grip portion 2 having a longitudinal axis 2A. As will be seen from FIG. 2, the user grips the grip portion by his hand and lightly presses the massager onto his head.

A pair of arms 3 extend laterally from the end of the main body 1 opposite to the grip portion 2. These arms 3 are spaced from each other by a suitable distance along the axis 1A of the main body 1. In the illustrated embodiment, the arms 3 are made hollow and are provided in their opposing surfaces 3A with slots 13 which extend laterally.

The arms 3 rotatably support both axial ends of a roller member 4 such that the roller member 4 is spaced from a curved surface 9 of the main body 1. The roller member 4 is rotatable about an axis 4A which, in the illustrated embodiment, extends substantially in parallel to the axis 1A of the main body 1. Pins 6 which are substantially coaxial with the axis 4A are provided on both axial ends of the roller member 4. These pins 6 project into the adjacent arms 3 through respective slots 13.

A coiled compression spring 12 is loaded between each pin 6 and a pin 14 provided in each arm 3. Thus, both pins 6 and, hence, both axial ends of the roller member 4 are urged outwardly, i.e., away from the main body 1.

Although not exclusively, the roller member 4 has a barrel-like or cylindrical form and is provided on the peripheral surface therof with a multiplicity of stimulating projections 5 which can have various configurations suitable for stimulating the scalp. In the illustrated embodiment, the projection 5 has a pyramidal form with a substantially square cross-section.

Figure 3:
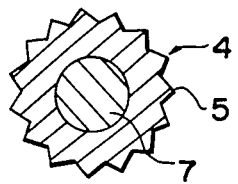
FIG. 3 is a cross-sectional view of a roller member incorporated in the scalp massager shown in FIG. 1.

A permanent magnet 7 may be embedded in the roller member 4 as shown in FIGS. 1 and 3. The use of such a permanent magnet 7 is preferred because the permanent magnet provides a magnetic stimulating effect which assists the physical stimulation imparted by the roller member to enhance the massaging effect. The roller member 4 is preferably of split type so that it may be split into halves along a parting line 11, thus enabling the permanent magnet 7 to be installed inside the roller member 4. The main body 1 also is of split type so that it can be split into halves along the longitudinal axis thereof. Preferably, the main body 1 is made of a plastic so that two halves are adjoined together by means of, for example, a bond.

It is also preferred that the axis 4A of rotation of the roller member 4 is inclined at an angle $\theta$ with respect to the longitudinal axis 2A of the grip portion 2. The angle $\theta$ is determined such as to enable the user to easily put the massager on his head in a manner shown in FIG. 2.

Figure 2:
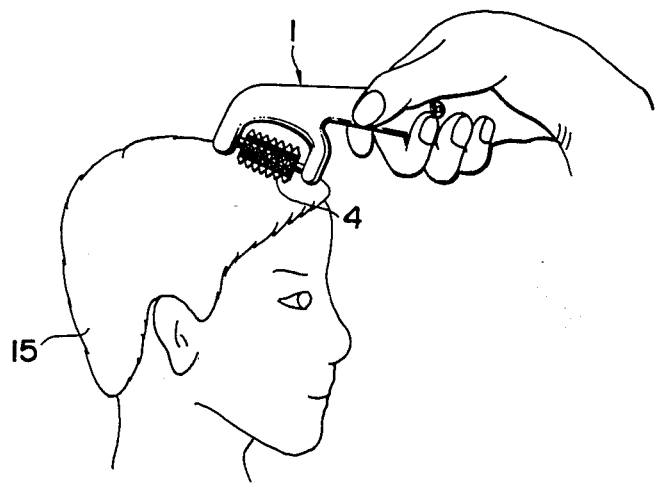
FIG. 2 is an illustration of the scalp massager shown in FIG. 1 in the state of use.

More specifically, the user holds the massager at the grip portion 2 and lightly presses the roller member 4 onto his head 15 and moves the massager back and forth and to the left and right as shown in FIG. 2, so that the roller member 4 rolls on the head 15. During rolling of the roller member 4, the projections 5 stimulate the scalp so as to enhance the blood stream under the scalp. Since the stimulation effect is imparted by the projections which are pressed with moderate force in accordance with the rotation of the roller member 4, there is no risk for the scalp to be damaged during massaging.

In addition, the roller member 4 softly contacts the head by virtue of the resilient displacement of the rolling member 4 towards the main body 1 against the force of the compression springs 12.

It will be clear to those skilled in the art that the scalp massager having the described construction can be produced without substantial technical difficulty.

Although the invention has been described through its preferred form, it is to be understood that the described embodiment is only illustrative and various changes and modifications may be imparted thereto.

Figure 4:
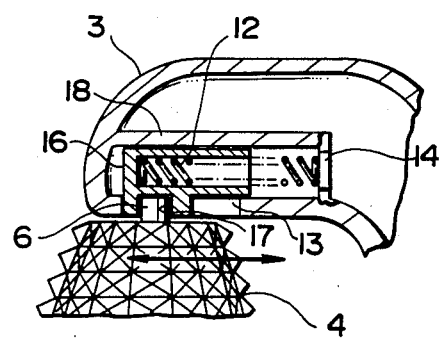
FIG. 4 is a modification of the embodiment shown in FIG. 1.

FIG. 4 shows a modification of the embodiment shown in FIG. 1. In this modification, a guide frame 16 is movably mounted in each arm 3. The guide frame 16 has a recess 17 which rotatably receives the adjacent pin 6 of the roller member 4. The portion of the guide frame 16 defining the recess 17 is slidably guided by a slot 13, while other portion of the guide frame 16 is guided by a guide portion provided in the arm 3. A compression spring 12 is loaded between the guide frame 16 and a spring retainer portion 14 in the arm 3. This arrangement enables the roller member 4 to move more smoothly and stably.

The coiled compression springs, which are used in the described embodiment for the purpose of resiliently urging the roller member, may be substituted by any other suitable biasing means capable of resiliently biasing the roller member.

Other changes and modifications are possible without departing from the scope of the invention which is limited solely by the appended claims.

What is claimed is:

1. A scalp massager comprising:
   a main body having a base portion with a longitudinal axis and a grip portion rearwardly extending from said base portion with an axis inclined with respect to said longitudinal axis;
   a pair of hollow supporting arms projecting forwardly and laterally from said base portion and spaced from each other in the longitudinal direction of said base portion, each arm having a slot;
   a roller member rotatably mounted between said arms for rotation about an axis substantially parallel to said longitudinal axis of said base portion, said roller member being provided on the outer peripheral surface thereof with scalp stimulating projection means and said roller member being provided at each longitudinal end with a pin, said pins being slidable along and projecting through said slots, respectively, into said hollow arms; and
   resilient means disposed within said hollow arms for resiliently biasing said roller member forwardly.

2. A scalp massager according to claim 1, wherein said roller member has a cylindrical form.

3. A scalp massager according to claim 1, wherein said axis about which said roller member rotates is inclined with respect to the longitudinal axis of said grip portion such as to facilitate the placement of said roller member on the head of the user who grips said grip portion.

4. A scalp massager according to claim 1, wherein said roller member has a barrel-like form.

5. A scalp massager according to claim 4, further comprising a permanent magnet disposed within said roller member.

6. A scalp massager according to claim 1, wherein a retaining pin is disposed within each of said hollow arms, and said resilient means includes a coiled compression spring loaded between said retaining pin and said pin of said roller member.

7. A scalp massager according to claim 6, wherein said coiled compression spring is disposed in a guide frame provided between said retaining portion in each arm and said pin on the adjacent end of the shaft of said roller member.

8. A scalp massager according to claim 1, wherein said projection means include a multiplicity of projections formed on the outer peripheral surface of said roller member.

9. A scalp massager according to claim 8, wherein each of said projections has a pyramidal form with a substantially square cross-section.

* * * * *